(12) United States Patent
Shor

(10) Patent No.: US 7,153,457 B2
(45) Date of Patent: Dec. 26, 2006

(54) METHOD FOR PROVIDING CUSTOM FIT THERAPEUTIC FOOTWEAR

(75) Inventor: Robert I. Shor, Coral Springs, FL (US)

(73) Assignee: Surefit, Inc., Coral Springs, FL (US)

( * ) Notice: Subject to any disclaimer, the term of this patent is extended or adjusted under 35 U.S.C. 154(b) by 969 days.

(21) Appl. No.: 09/976,071

(22) Filed: Oct. 15, 2001

(65) Prior Publication Data

US 2003/0073944 A1 Apr. 17, 2003

(51) Int. Cl.
B29C 00/00 (2006.01)
B28B 1/48 (2006.01)
A43D 00/00 (2006.01)

(52) U.S. Cl. ............ 264/40.1; 264/156; 264/553; 12/146 M; 12/146 B; 12/142 N

(58) Field of Classification Search ............ 264/40.1, 264/553, 155, 156; 12/146 M, 142 N, 146 B
See application file for complete search history.

(56) References Cited

U.S. PATENT DOCUMENTS 2,401,946 A * 6/1946 Littlefiield ............ 264/156
4,503,576 A * 3/1985 Brown .................. 12/146 M
4,674,204 A * 6/1987 Sullivan et al. ........ 264/244
4,756,096 A * 7/1988 Meyer .................. 12/142 N
4,803,747 A * 2/1989 Brown .................. 12/142 N
5,237,520 A * 8/1993 White .................. 12/142 N
6,042,759 A * 3/2000 Marshall ................ 264/40.1
6,238,602 B1 * 5/2001 Liu ...................... 264/40.1
6,523,206 B1 * 2/2003 Royall .................. 12/142 N
2002/0158358 A1 * 10/2002 Franzene ................ 264/40.1

* cited by examiner

Primary Examiner—Ted Kavanaugh
(74) Attorney, Agent, or Firm—Dennison, Schultz, Dougherty & MacDonald

(57) ABSTRACT

A method for manufacturing custom fit therapeutic footwear such as shoes and inserts includes the step of measuring a patient's foot and forming an imprint of a patient's foot to identify the patient's footprint and any high pressure areas on the bottom of the foot. The method also includes the step of making a mold of a lower portion of the patient's foot and subsequently making a plaster cast of the lower portion of the patient's foot. A multidensity sheet of insert material is provided and formed into a shape that corresponds to the lower portion of a patient's foot as for example by vacuum forming. The method also includes the step of providing a second insert material that is softer than the first insert material. The imprint of the patient's foot is then used to position any needed accommodations. The area to be accommodated is then punched out through the entire thickness of the insert and filled with a sheet of softer insert material. The final product may then be covered with a top coat or sheet of moldable polyethylene.

14 Claims, 3 Drawing Sheets

METHOD FOR PROVIDING CUSTOM FIT THERAPEUTIC FOOTWEAR

FIELD OF THE INVENTION

This invention relates to a method of remotely fitting therapeutic footwear and manufacturing custom molded inserts with accommodations to meet the needs of diabetics and other individuals with a need for custom fit therapeutic shoes and inserts, and to custom fit therapeutic inserts.

BACKGROUND FOR THE INVENTION

Podiatrists and other licensed professional practitioners such as orthotists, pedorthotists, and chiropractors have for some years provided therapeutic footwear for diabetics and other patients with a need for custom fitted therapeutic shoes and inserts. However, such practices have often proven unsatisfactory, time consuming and frequently less profitable than desired. The problem is that the practice is time consuming and frequently results in inconsistencies and poorly fitting shoes and inserts, a necessity to replace poorly fitting shoes and more recently to comply with the requirements of Medicare and other health care providers.

It is also common practice for licensed professional practitioners to measure a patient's foot, make a mold of a lower portion of the foot and ask a laboratory or manufacturer to make a custom fit therapeutic insert for placement in a shoe. Such laboratories typically work with a mold of a patient's foot, form a plaster cast from the mold and based on an examination of an imprint add or build up material on the plaster cast to provide an indentation when an insert is formed from the cast. In the past, such practices have led to poorly fitting accommodations and less than satisfactory inserts.

It is presently believed that there is a need for and/or a relatively large market for an improved method for providing custom fit therapeutic footwear, i.e. shoes and inserts for diabetic and other patients. There is a need because the improved methods disclosed herein minimize the work of a licensed professional practitioner, result in improved or better fitting shoes and inserts, reduce shoe and insert returns and needs for refitting and provide more accurate accommodations, all at a competitive cost.

BRIEF SUMMARY OF THE INVENTION

In essence, the present invention contemplates a method for manufacturing custom fit therapeutic footwear for diabetic and other patients with a need for custom fit therapeutic shoes and inserts. The method includes the step of measuring a patient's foot and forming an imprint of a patient's foot to identify the patient's footprint and any high pressure areas on the bottom of the foot. The method also includes the step of making a mold of a lower portion of the patient's foot and subsequently making a cast such as a plaster cast of the lower portion of the patient's foot from the mold. A mass of a first insert material, preferably a multi-layer sheet of heat moldable polyethylene foam material is provided and formed into a shape that corresponds to the patient's foot as for example by vacuum forming. The insert is then sanded to fit the contours of the foot and shoe.

The method also includes the step of providing a mass of a second insert material, preferably a polyurethane material that is softer than the first insert material. The imprint of the patient's foot is then used to position any needed accommodations. For example, the insert is positioned over the first imprint after highlighting those areas to be accommodated with an ink marker. The area to be accommodated is then punched out through the entire thickness of the insert as for example with a metal punch. The hole is then at least partially filled with a softer second insert material. The final product is then covered with a top coat or sheet of moldable polyethylene foam material.

In a preferred embodiment of the invention, the steps of measuring and imprinting a patient's foot and making a mold of the foot are performed by or under the supervision of a licensed professional practitioner. The forming of a plaster positive cast and insert are then performed at a laboratory which delivers custom fit shoes and inserts to the licensed professional practitioner for dispensing to the patient.

The invention will now be described in connection with the accompanying drawings.

DESCRIPTION OF THE PREFERRED EMBODIMENTS OF THE INVENTION

The following embodiments of the present invention are designed to make it easy for a podiatrist or other licensed professional practitioner to provide footwear that meets the unique needs of their diabetic patients. They can meet these needs by supplying footwear that treats the lower extremity complications of diabetes. The methods disclosed herein facilitate the work of a podiatrist, improves the outcome of their diabetic patients and at the same time allows much of the work to be done by a technician under the podiatrist's supervision. The method also provides for the manufacture of such items to be done by an outside laboratory or manufacturer of custom inserts. The methods disclosed herein also facilitate qualifying patients, meeting the requirements of Medicare and other health care providers in obtaining better fitting shoes and inserts at a competitive price.

Figure 1:
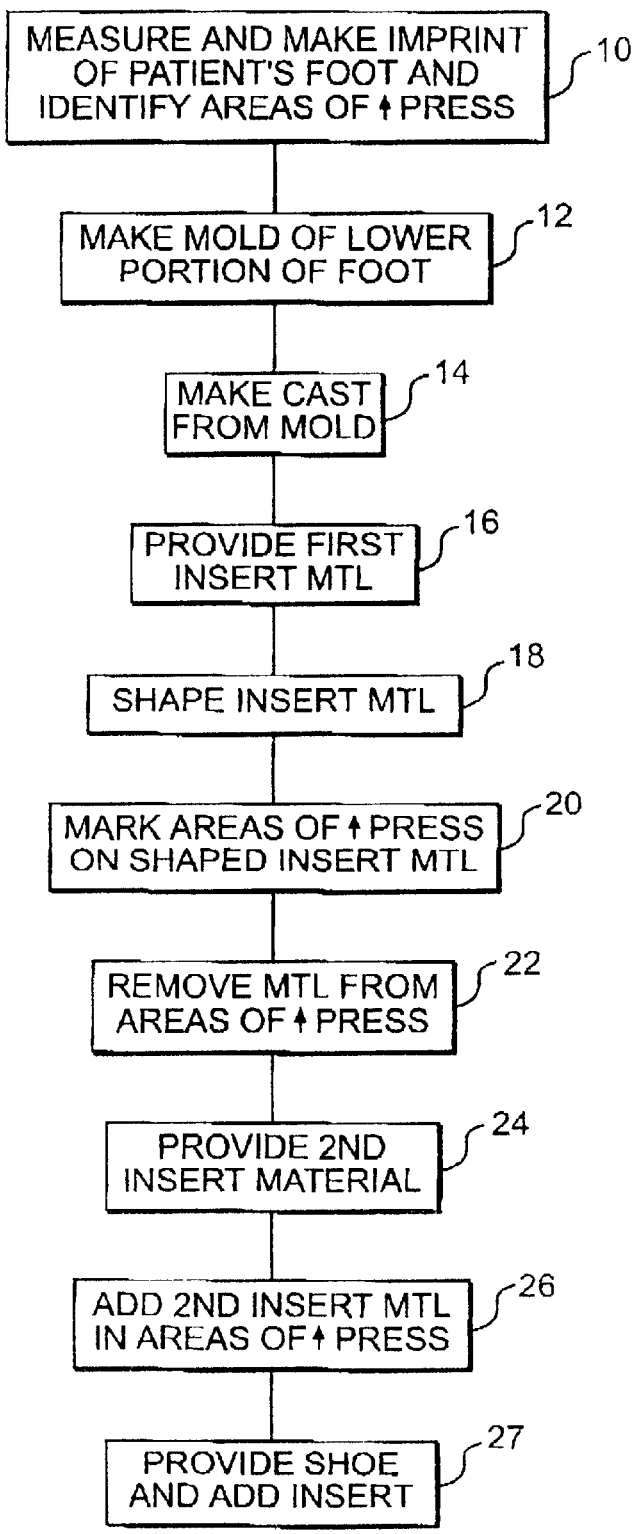
FIG. 1 is a block diagram which illustrates a first embodiment of the invention.

The method in accordance with a first embodiment of the invention will now be described in connection with FIG. 1. As shown therein, the step 10 calls for a licensed professional practitioner or their medical technician to measure and make an imprint of a patient's foot and at the same time identify areas of high pressure.

Measuring the patient's foot is normally done with a conventional Brannock device. These measurements should be taken with the patient wearing the socks that they will normally wear with the shoes. Three different measurements are taken: the heel to toe length, heel to ball length (or arch length) and the width. In taking these measurements, it is desirable to use a counter for support. The patient stands with both feet together with the right foot closest to the counter. The Brannock device is placed to the left of the patient's left foot and the patient picks up his left foot and places his left heel on the area of the device that is marked left heel. The feet should be side by side with the heel of the foot placed as far back in the device as possible. Next, the foot is positioned so it is resting against the heel to ball measuring device. There should be no space between the foot and the heel to ball measuring device. The width measuring device is then slid against the outside of the foot (the lateral aspect of the foot.)

While standing in front of the patient, the licensed professional practitioner or technician looks straight down over the foot to obtain the heel to toe length for the longest toe. Viewing at an angle could cause an inaccurate reading. The longest toe is usually the first or second toe but on rare occasions the third toe may be the longest. If the longest toe comes out on the line marked 8, record the heel to toe length as an 8. However, if the heel to toe length measures between a 7½ and an 8, record the heel to toe length as 7½ plus.

After measuring the heel to toe length, it is necessary to make a heel to ball measurement. With the left foot still in the device, obtain the heel to ball length by making sure the heel to ball measuring device (arch length measuring device) is next to the widest part of the foot at the ball (i.e. the device is rounded and should encircle the medial aspect of the first met head). This number is recorded.

The width is then measured making sure that the width measuring device is against the outside (lateral aspect) of the foot. The patient is then turned around and positioned so that the Brannock device is to the right side of the patient's right foot and the aforementioned steps are repeated.

After measuring the foot with the Brannock device, the foot is removed from the device. The patient continues to stand with their socks on and the circumference of the widest part of the foot at the ball is measured with a measuring tape. The measurement is made from floor to floor on the medial side of the first met head over the top of the foot and down to the floor on the lateral side of the $5^{th}$ met head. The technician should make certain that the tape measure is not pulled too tightly against the foot. This measurement is recorded for each foot.

After measuring the foot, a conventional foot imprinter is used to obtain a tracing of the foot and to identify any pressure points on the bottom of the foot. In practice, a conventional foot imprinter is opened and includes a rubber mat having a smooth side and a side with a grid or crosshatch pattern on it. Several drops of ink are disposed onto the side of the rubber mat that has the grid pattern on it. No ink should be applied to the smooth side of the mat. Thus, the patient will not get any ink on his feet because he will be stepping on the smooth side of the mat only. Spread the ink with a roller. Press firmly back and forth with the roller until the ink has been spread uniformly over the entire rubber sheet. When finished, the roller is placed on a paper towel. The mat is then re-inked when foot imprints become light.

A piece of legal sized paper is placed in the imprinter on the side next to the rubber mat and the rubber mat is flipped over onto the paper with the smooth side of the mat facing up. The ink side should be facing down on top of the paper. Then, when the patient steps onto the mat, the ink will show up on the paper.

At this point, the patient stands next to the counter for support and faces the technician with their right foot closest to the counter. The foot is placed on the imprinter next to the patient's left foot with the rubber mat of the imprinter next to the left foot. The patient then lifts their left foot and the technician guides it to the center of the rubber mat. With the left foot on the rubber mat, the technician traces an outline of the foot with a blunt object such as a pen with the point retracted. The pen should be held at 90° to the foot and pressed down so that the outline of the foot comes out on the paper underneath the mat. Then, the patient takes a small step forward with the right foot and steps off the mat by lifting their left heel and stepping forward. This procedure is done to obtain a good imprint of any pressure points on the fore foot. The piece of paper from the imprinter is removed and has the footprint and tracing on it. Another blank sheet of legal size paper is then placed in the imprinter and the rubber mat is placed on top of the new piece of paper. The patient is then turned in the opposite direction and the previous steps repeated.

The pressure points indicated on the imprint are then circled for accommodation.

The licensed professional practitioner or their technician also makes a foam impression of the patient's foot in step 12. Impressions are preferably done using a 14 inch foam box. Once again, the patient is asked to stand next to a counter with both feet together with the right foot closest to the counter. The foam impression box is opened and a line marked with a pencil 1 inch from the back edge of the foam on both foam sections. This line mark is used to position the back of the heel.

With the technician standing in front of the patient, the foam box is moved next to the patient's left foot and the patient's left heel is guided onto the 1 inch mark without pressing into the foam. The foot is then held in a neutral position by grasping just below the ankle bone with the technician's thumb and index finger on one hand. At the same time with the other hand apply 2 or 3 fingers on the first metatarsal. While holding the patient's foot in this position, the patient applies downward pressure on the foam material until they meet resistance, the ankle and first metatarsal are held firmly as the impression is being made to avoid tilting of the foot. After the impression has been made and before removing the foot from the foam, the technician firmly pushes down the ends of the toes so that they are not elevated (dorsiflexed). The foot is then removed from the foam, the patient turned in the opposite direction and the foam box is then placed next to right foot and an impression made in the same manner.

The mold imprint and measurements together with the doctor's patient evaluation and foot imprints are then forwarded to the laboratory or manufacturer.

The custom orthotic fabrication process incorporates the impression of the patient's foot from the aforementioned foam block or plastic slipper cast. Once this is received, the fabrication process begins with step 14 by pouring liquid plaster of paris into the impression and waiting for it to harden. Once hardened, the cast is sanded smooth in a manner that is consistent with standard orthotic lab procedures for the fabrication of an accommodated orthotic.

In step 16, a first insert material is provided for example a dual density material consisting of 2 laminated layers of Plastazote material which is a heat moldable polyethylene foam material. The top layer is preferably a 20 durometer medium density Plastazote while the bottom layer or shell is about 35 durometer firm density Plastazote. The medium density top layer of Plastazote material ranges in thickness from ⅛ to ¼ inch and the bottom layer of firm density ranges in thickness from ¼ to ½ inch depending on the arch height, heel shape and other factors.

This material which is provided in sheets with 2 layers laminated together is cut to a size that is slightly larger than the foot and placed in a convection oven at 250° F. for 2 to 3 minutes until soft. Then the material is placed over the cast which is lying inside a vacuum forming machine with the bottom of the cast (bottom of foot) facing upwards. The vacuum forming machine is closed and the heated material is pulled down over the cast as the air is removed from the vacuum forming chamber to thereby shape the insert material in step 18. The insert is then ground to fit the shape and contour of the shoe and foot.

When the insert is completed, a technician trained in making accommodations applies the accommodation that was ordered. The technician uses the ink imprint for positioning the accommodation on the device. The high pressure areas are highlighted on the imprint with a wet ink marker. Then the insert is positioned by lining up the heel cup of the device with the traced outline of the heel on the foot imprint. In step 29, the highlighted area is transferred to the insert by applying pressure to the insert while it is precisely located over the imprint. The area to be accommodated is then punched out through the entire thickness of the insert using a metal punch of the correct diameter in step 22. The punches used range from 3/8 of an inch to 1½ inches. The size of the punch used is determined by measuring the diameter of the high pressure areas that are present on the imprint. A second insert material is provided in step 24. Once the hole is punched in the insert, the hole is partially filled in (See step 26) with the second insert material, preferably a sheet of Poron i.e. a 15 durometer polyurethane material that is softer than the Plastazote. The Poron material that is provided is 1/16 to 1/8 inch in thickness depending on the thickness of the hole that is present. The final product is then covered with a top coat of 1/16 inch 20 durometer medium density Plastazote to enclose the pocket and finish the device. The insert is then added to or coupled with a shoe and dispensed to a patient in step 27.

The imprint formed in step 10 is also used in shoe sizing. The foot imprint is used to confirm the preliminary size based on the use of the Brannock device. For example, a removable manufactured insole of the preliminary length and width is placed as a template on top of the foot imprint for comparison. The heel cup of the insert is aligned with the tracing outline of the heel on the imprint. Then a line is drawn around the insert template and compared to the tracing outline on the imprint. It is then determined whether there is adequate length and width to accommodate the foot. An adequate length is determined when the template covers the toes with ½ inch allowance beyond the end of the longest toe. An adequate width is determined by complete coverage of the foot imprint across the ball of the foot. If length and width is inadequate, a series of progressively larger templates are placed over the imprint until a satisfactory match is obtained and the proper size is determined.

Figure 2:
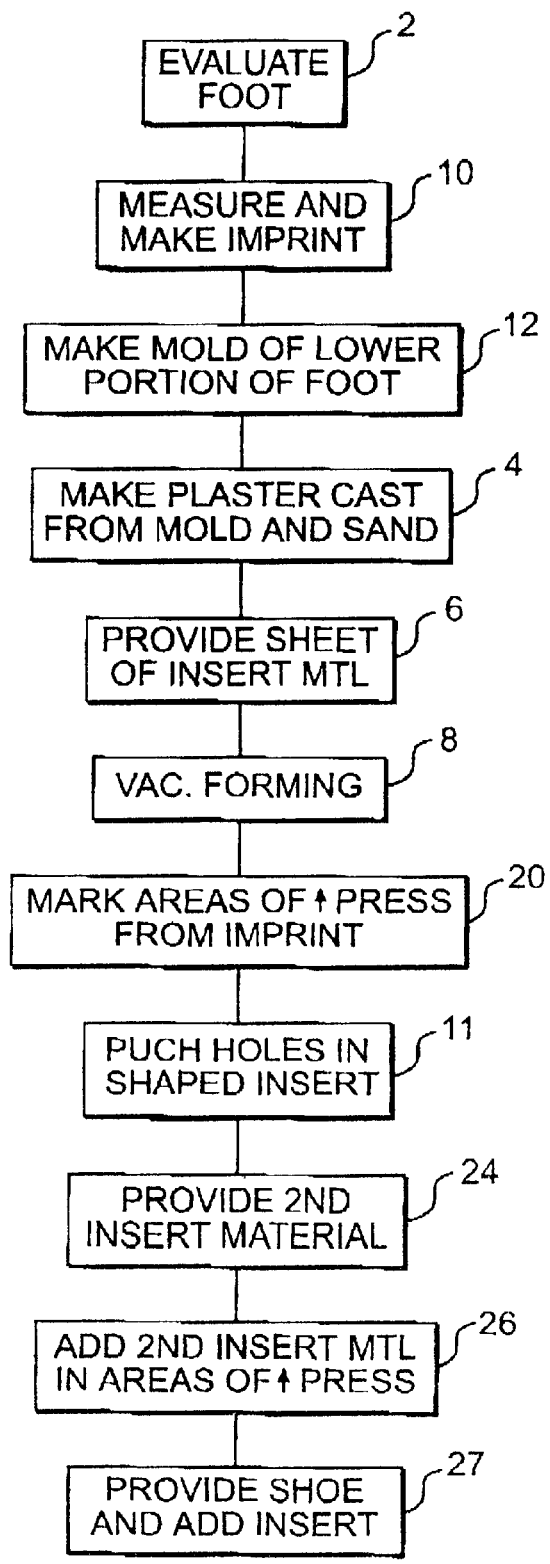
FIG. 2 is a block diagram which illustrates a second embodiment of the invention.
Figure 3:
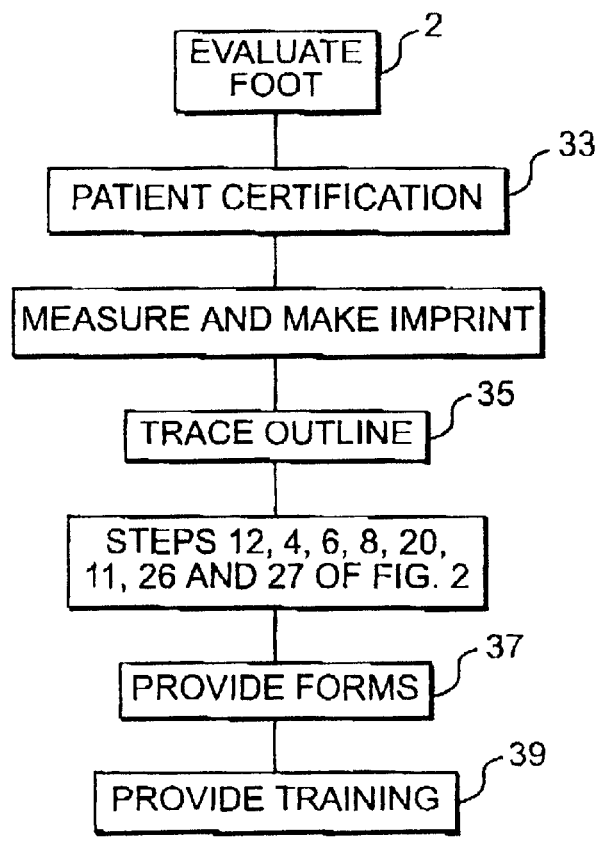
FIG. 3 is a block diagram which illustrates another embodiment of the invention.
Figure 4:
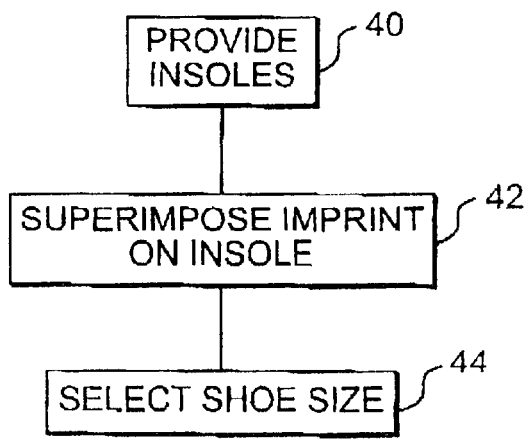
FIG. 4 is a block diagram which illustrates a further embodiment of the invention.

As illustrated in FIG. 2, the method of providing therapeutic footwear for diabetics and other patients includes an initial step 2. In the initial step the licensed professional practitioner examines the patient's foot for problems and notes problems such as amputation of a part of either foot, foot ulceration, pre-ulcerative callouses, peripheral neuropathy, foot deformity or poor circulation. The method also includes the steps 10 and 12 as described in connection with FIG. 1. A step 4 is similar to step 14 but is done by forming a plaster cast and subsequently smoothing the plaster cast as for example by sanding to a smooth finish. Step 6 of the second embodiment of the invention is generally similar to step 16 of the first embodiment of the invention, however, the mass of first insert material is a multilayer laminated sheet of a foam polyethylene. This multilayer sheet of polyethylene foam is then shaped in step 8 by vacuum forming. The insert material is then cut to a size which is larger than the foot and heated in a convection oven at about 250° F. for two to three minutes until soft. Then the material is placed on the cast which is placed in a vacuum forming machine with the bottom of the cast facing upwards. The vacuum forming machine is closed and the heated insert material is pulled down over the cast as the air is removed from the vacuum forming chamber. The insert is then ground to shape to fit the shape and contour of the shoe and last.

After the basic insert is made, the imprint which if prepared in step 10 is used to make any needed accommodations as defined above with respect to the first embodiment of the invention. In a final step 27, the licensed professional practitioner dispenses the shoes to the patient, tests them for fit and completes any insurance forms and other paperwork which is necessary.

In the third embodiment of the invention the procedure follows the general approach of the second embodiment of the invention. However, includes step 33 of patient certification and charting. In order to comply with Medicare and other requirements a statement of a certifying physician as recommended by the durable medical equipment carriers is completed. The third embodiment of the invention also incorporates the step 35 of tracing an outline of a foot on the imprint. Then follows the general procedures from FIG. 2 and adds the steps 37 and 39 of providing forms to the licensed professional practitioner as well as training for the practitioners technicians.

The fourth embodiment of the invention incorporates steps 10, 12, 14, 16 and 18 from the first embodiment of the invention.

It then adds the step 40 of providing insoles based on measurements obtained by the podiatrist. The foot imprint is used to confirm the preliminary size in step 42. For example, a removable manufacturer's insole of the preliminary length and width is placed as a template on top of the foot imprint for comparison. The heel cup of the insert is aligned with the tracing outline of the heel on the imprint. Then a line is drawn around the insert template and compared to the tracing outline on the imprint. It is then determined whether there is adequate length and width to accommodate the foot. An adequate length is determined when the template covers the toes with one-half inch allowance beyond the end of the longest toe. An adequate width is determined by complete coverage of the foot imprint cross the ball of the foot. Is length and width is inadequate a series of progressively larger templates are placed over the imprint until a satisfactory match is obtained and the proper size is determined. Based on the above the appropriate size of the shoe is selected in step 44, the insert added or shipped separately and the shoes and inserts dispensed to the patient.

A further embodiment of the invention contemplates a fitted molded therapeutic insert which meets the needs of diabetics and other individuals with a need for custom fitted therapeutic inserts. The inserts include a multidensity molded base having a shape which corresponds to the bottom of a patient's foot. That base has a length, width and thickness and defines an opening passing completely through the thickness of the base and defining an area which corresponds to high pressure points on the bottom of a patient's foot. A plastic insert material which is softer then the molded base at least partially fills the opening. The plastic insert material is essentially the same size as the opening but has a thickness which is preferably less than the thickness of the base. A medium density layer conforming to the shape of a patient's foot covers the molded base and the at least partially filled opening to complete the insert.

In a preferred form, the insert is made of a multidensity heat moldable material such as polyethylene with a top layer of about 20 durometer hardness and a bottom layer of about 35 durometer hardness. The plastic insert material is made of a polyurethane with a hardness of about 15 durometer while the medium density layer is a polyethylene material with a hardness of about 20 durometers.

While the invention has been described in connection with its accompanying drawings, it should be recognized that changes and modifications may be made therein without departing from the scope of the appended claims.

What is claimed is:

1. A method for manufacturing custom fit therapeutic footwear inserts comprising the steps of:
   a) measuring and imprinting a patient's foot to identify a patient's footprint and high pressure areas on the bottom of the foot;
   b) providing a multidensity first insert that is fabricated from a mold of the foot;
   c) forming an opening in and passing through the first insert corresponding to at least one of the high pressure area;
   d) providing a mass of a second insert material having a softer hardness then the first insert material; and,
   e) closing the opening in the first insert material with a mass of the second insert material and covering the top of the insert with a third mass to provide a custom molded insert with accommodations.

2. A method for manufacturing custom fit therapeutic footwear according to claim 1 which includes the step of inserting the custom fit inserts into a shoe.

3. A method for manufacturing custom fit therapeutic footwear according to claim 2 in which the opening formed in step c is formed by punching a hole in the insert.

4. A method for manufacturing custom fit therapeutic footwear comprising the steps of:
   a) measuring and imprinting a patient's foot to identify a patient's footprint and high pressure areas on the bottom of the foot;
   b) making a mold of a lower portion of the patient's foot and forming a cast of the lower portion of the patient's foot from the mold;
   c) providing a first insert multidensity material and forming the mass into a shape that corresponds to the patient's foot;
   d) forming an opening in and passing through the first insert material corresponding to at least one of a high pressure areas identified on the imprint of the patient's foot;
   e) providing a mass of a second insert material having a softer hardness then the first insert materials; and,
   f) at least partially filling the opening in the first insert material with a mass of the second insert material to thereby provide a custom fit insert.

5. A method for manufacturing custom fit therapeutic footwear according to claim 4 which includes the step of measuring the patient's foot, selecting a manufactured shoe to fit the patient's foot and inserting the custom fit insert into the selected shoe.

6. A method for manufacturing custom fit therapeutic footwear according to claim 5 which includes the steps of tracing an outline of the patient's foot on the imprint and sizing a shoe based on the outline of the patient's foot.

7. A method for manufacturing custom fit therapeutic footwear according to claim 6 in which the steps of imprinting a patient's foot is made by a patient's stepping off of the imprint.

8. A method for manufacturing custom fit therapeutic footwear according to claim 7 which includes the steps of vacuum forming the first insert material and providing a sheet of the second insert material which is cut out to fit the opening in the first insert material.

9. A method for remotely fitting therapeutic footwear and manufacturing custom molded inserts with accommodations comprising the steps of:
   a) evaluating a patient's foot;
   b) measuring and imprinting a patient's foot to identify a patient's footprint and high pressure areas on the bottom of the foot;
   c) making a mold of a lower portion of the patient's foot;
   d) forming a smooth cast of the lower portion of the patient's foot from the mold;
   e) providing a mass of a first insert material having two different durometers and forming the mass into a shape that corresponds to the lower portion of the patient's foot;
   f) punching hole in the shaped first insert material corresponding to at least one of the high pressure areas on the imprint of the patient's foot;
   g) providing a sheet of a second insert material having a durometer that is softer than the first insert materials;
   h) at least partially filling the opening in the first insert material with a cut out portion of the second insert sheet to thereby form a custom fit insert;
   i) dispensing shoes and custom inserts to the patient; and
   wherein steps a, b, c and i are performed in the offices of a licenses professional practitioner and steps d, e, f, g and h are performed in a laboratory for manufacturing custom fit inserts.

10. A method for remotely fitting therapeutic footwear and manufacturing custom molded inserts with accommodations according to claim 9 which includes the steps of certifying a patient for therapeutic footwear, charting a patient's need for shoes and inserts and prescribing shoes and inserts and/or wherein such steps are performed by the office of a licensed professional practitioner.

11. A method for remotely fitting therapeutic footwear and manufacturing custom molded inserts with accommodations according to claim 9 which includes the step of tracing an outline of a patient's foot on the imprint.

12. A method for remotely fitting therapeutic footwear and manufacturing custom molded inserts with accommodations according to claim 11 which includes a further step of training by the laboratory of personnel in the offices of the licensed professional practitioner.

13. A method for remotely fitting therapeutic footwear and manufacturing custom molded inserts with accommodations according to claim 12 wherein the laboratory provides the licensed professional practitioner with forms and instructions for documenting patient evaluation, certifying and insurance billing for custom fit therapeutic footwear.

14. A method for remotely fitting therapeutic footwear and manufacturing custom molded inserts with accommodations according to claim 9 in which step a) includes a determination of whether the patient has diabetes mellitus and one or more of the following conditions; previous amputation of a foot or part of a foot, previous ulceration, history of pre-ulcerative callouses of either foot, peripheral neuropathy, foot deformity or poor circulation in a foot.

* * * * *